United States Patent
Hirabayashi et al.

(10) Patent No.: US 9,192,593 B2
(45) Date of Patent: Nov. 24, 2015

(54) AMINO-ACID CONTAINING COMPOSITION FOR INHIBITING ACCUMULATION OF FAT

(75) Inventors: Yuri Hirabayashi, Kawasaki (JP); Hitoshi Murakami, Kawasaki (JP); Hisamine Kobayashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1083 days.

(21) Appl. No.: 11/847,939

(22) Filed: Aug. 30, 2007

(65) Prior Publication Data

US 2008/0058264 A1   Mar. 6, 2008

(30) Foreign Application Priority Data

Aug. 30, 2006   (JP) .................. 2006-234155

(51) Int. Cl.
| | |
|---|---|
| A23K 1/18 | (2006.01) |
| A23J 1/00 | (2006.01) |
| A01N 43/60 | (2006.01) |
| A61K 31/525 | (2006.01) |
| A01N 37/00 | (2006.01) |
| A61K 31/19 | (2006.01) |
| A01N 35/00 | (2006.01) |
| A61K 31/12 | (2006.01) |
| A61K 31/197 | (2006.01) |
| A61K 38/02 | (2006.01) |
| A61K 38/05 | (2006.01) |
| A61K 38/06 | (2006.01) |
| A61K 38/07 | (2006.01) |
| A61K 38/08 | (2006.01) |
| A61K 38/10 | (2006.01) |
| A61K 38/16 | (2006.01) |

(52) U.S. Cl.
CPC ............. *A61K 31/197* (2013.01); *A61K 38/02* (2013.01); *A61K 38/05* (2013.01); *A61K 38/06* (2013.01); *A61K 38/07* (2013.01); *A61K 38/08* (2013.01); *A61K 38/10* (2013.01); *A61K 38/16* (2013.01)

(58) Field of Classification Search
USPC ................ 426/656, 2; 514/251, 557, 675, 54
See application file for complete search history.

(56) References Cited

U.S. PATENT DOCUMENTS

| | | | | |
|---|---|---|---|---|
| 3,518,243 | A | * | 6/1970 | Bertellini et al. ............. 530/395 |
| 5,242,697 | A | * | 9/1993 | Luca .............................. 426/231 |
| 5,268,360 | A | * | 12/1993 | Yoshikawa et al. ............. 514/18 |
| 2002/0106436 | A1 | * | 8/2002 | Gohman et al. ............... 426/590 |
| 2003/0185876 | A1 | * | 10/2003 | Calton et al. .................. 424/439 |

(Continued)

FOREIGN PATENT DOCUMENTS

| | | |
|---|---|---|
| JP | 63-30411 | 2/1988 |
| JP | 03219838 A * | 9/1991 |

(Continued)

OTHER PUBLICATIONS

Reference Guide for Amino Acids (Jan. 31, 2001) available at http://www.realtime.net/anr/aminoacd.html.*

(Continued)

*Primary Examiner* — Rena L Dye
*Assistant Examiner* — Assaf Zilbering
(74) *Attorney, Agent, or Firm* — Oblon, McClelland, Maier & Neustadt, L.L.P.

(57) ABSTRACT

An amino-acid containing composition for inhibiting accumulation of fat, containing leucine in an amount of 33 to 67% by weight and threonine in an amount of 33 to 67% by weight, in terms of free amino acids thereof, based on whole amino acids.

16 Claims, 8 Drawing Sheets

(56) References Cited

U.S. PATENT DOCUMENTS

| | | | |
|---|---|---|---|
| 2005/0106220 A1* | 5/2005 | Inagawa et al. | 424/442 |
| 2005/0249781 A1 | 11/2005 | Hirabayashi et al. | |

FOREIGN PATENT DOCUMENTS

| | | |
|---|---|---|
| JP | 04-346770 | 12/1992 |
| JP | 06-024977 | 2/1994 |
| JP | 09-157163 | 6/1997 |
| JP | 2003-048830 | 2/2003 |
| JP | 2004-262848 | 9/2004 |
| JP | 2004-315384 | 11/2004 |

OTHER PUBLICATIONS

Google search results with Reference Guide for Amino Acids date (Jul. 22, 2011).*
Threonine Google website pub. date (Apr. 21, 2012).*
Threonine from supplementalnews.org (Sep. 14, 2004).*
Horikawa et al. JP 03219838 A English abstract (1991).*
Storck et al., Metabolism of isolated fat cells from various tissue sites in the rat: influence of hemorrhagic hypotension, 200 Journal of Lipid Research vol. 15, p. 200-205 (1974).*
Buchowski et al., Plasma Leptin Association with Body Composition and Energy Expenditure in Sickle Cell Disease Maciej S. J Am Coll Nutr April vol. 19 No. 2 p. 228-236 (2000).*
Weisberg et al., Obesity is associated with macrophage accumulation in adipose tissue, The Journal of Clinical Investigation, vol. 112, No. 12 p. 1796-1808 (2003).*
Threonine Intro Wayback Machine Printout (May 19, 2006).*
Layman et al., Potential Importance of Leucine in Treatment of Obesity and the Metabolic Syndrome, J. Nutr. 136 p. 319S-323S (2006).*
Layman, The Role of Leucine in Weight Loss Diets and Glucose Homeostasis, J. Nutr. 133: p. 261S-267S (2003).*
Human Anatomy, Wikipedia website, printed from Wayback Machine website (Jul. 6, 2005).*
Albright et al., Adipose tissue. In Encyclopedia of Sports Medicine and Science, Internet Society for Sport Science (sportsci.org) (May 30, 1998).*
Donato et al., "Effects of leucine supplementation on the body composition and protein status of rats submitted to food restriction". Nutrition. vol. 22, pp. 520-527 (Feb. 2006).*
"The Lipotropic Effect of Threonine". Nutritional Review 12(5): pp. 151-152 (May 1954).*
"Weight Loss Aids" Available online at therapy.epnet.com on Apr. 1, 2005.*
Jose Donato, et al., "Effects of leucine supplementation on the body composition and protein status of rats submited to food restriction" Nutrition, vol. 22 (2006), (pp. 520-527).
Japanese Office Action issued Nov. 19, 2012 in corresponding Japanese Patent Application No. 2007-224063 with English translation (4 pp.).
Ballor, et al. The American Journal of Clinical Nutrition. "Resistance weight training during caloric restriction enhances lean body weight maintenance." 1988, vol. 47, pp. 19-25.
Weinheimer, et al. Nutrition Reviews. "A systematic review of the separate and combined effects of energy restriction and exercise on fat-free mass in middle-aged and older adults: implications for sarcopenic obesity." 2010, vol. 68 (7), pp. 375-388.

* cited by examiner

AMINO-ACID CONTAINING COMPOSITION FOR INHIBITING ACCUMULATION OF FAT

FIELD OF THE INVENTION

The present invention relates to an amino-acid containing composition for inhibiting accumulation of fat, comprising a particular combination of amino acids. More specifically, the present invention relates to an amino-acid containing composition for inhibiting accumulation of fat, characterized by comprising threonine alone in a particular proportion, or in combination with other amino acids in a particular proportion.

BACKGROUND OF THE INVENTION

Excessive accumulation of fat induces metabolic disorders. For example, when the fat is accumulated in the liver, muscles and blood to an excessive degree, fatty liver and insulin resistance will be induced. In addition, excessive fat accumulation in the fat cells will result in obesity. An increase in the number of obese people has constituted a serious social problem throughout the world. The accumulation of fat will thus cause various problems as mentioned above, so that it becomes the key to solving the problems to inhibit fat from being accumulated.

For preventing the accumulation of fat, to restrict the volume and kind of diet and to do exercise are found to be effective. However, the restriction of diet and the physical exercise need strong wills and efforts, so that those methods are not always practical for preventing the accumulation of fat. Accordingly, there has been an increasing demand for a method for preventing the accumulation of fat conveniently and effectively without any special exercise and restricted diet. Intake of supplements is now under consideration as one of the means for preventing the accumulation of fat. However, according to the reports about the currently used supplements, some have insufficient efficacy, and others have the potential for impairing the health, for example, impairing the liver function by the administration.

Amino acids are constituents of protein. The amino acids have been found to be highly safe from the long past experience of eating habits. In addition, it has become clear that the amino acids have a variety of physiological actions, in particular, an inhibitory effect on the fat accumulation. There are some reports regarding the mixtures of amino acids. For example, Japanese Patent Unexamined Publication (JP Kokai) Hei 6-24977 discloses that a mixture of thirteen kinds of amino acids can lower the body weight and the body fat; JP Kokai Hei 4-346770 discloses a mixture of eight kinds of essential amino acids can reduce the body fat; and JP Kokai Hei 9-157163 discloses an amino acid composition comprising nine kinds of essential amino acids, with arginine being contained in major proportions, can control obesity. The compositions of those amino-acid mixtures are shown in Table 2. There is also a report about the effect of an amino acid when used by itself, i.e., the promoting effect of leucine on the weight loss when leucine is taken during a period of restricted diet (Nutrition, 2006 May; 22 (5): 520-7). However, the methods disclosed in those documents require exercises or restriction of the food intake. Moreover, the above-mentioned methods are not compared and analyzed in the same manner, so that it has not been identified which composition has an action of sufficiently inhibiting the accumulation of fat. A more effective composition is desired.

SUMMARY OF THE INVENTION

An object of the present invention is to provide a composition comprising amino acids as the active ingredients that can give the effect of inhibiting the accumulation of fat safely, conveniently and maximally to ones who pay particular attention to the accumulation of fat in the fat tissue, liver and blood.

As a result of the intensive studies to solve the above-mentioned problems, the inventors of the present invention found that a composition containing particular amino acids in the particular proportions exhibits the action of inhibiting the accumulation of fat. In particular, the inventors found that a composition containing threonine alone in a particular proportion, or threonine in a particular proportion in combination with other amino acids in a particular proportions exhibits the action of inhibiting the accumulation of fat. The present invention has been thus accomplished.

Namely, the present invention provides an amino-acid containing composition for inhibiting accumulation of fat, comprising threonine in an amount of 33 to 67% by weight, in terms of free amino acids thereof, based on whole amino acids.

The present invention also provides an amino-acid containing composition for inhibiting accumulation of fat, comprising leucine in an amount of 33 to 67% by weight and threonine in an amount of 33 to 67% by weight, in terms of free amino acids thereof, based on whole amino acids.

The present invention also provides a food, supplement, drug, and feed, comprising the immediately above-mentioned amino-acid containing composition for inhibiting accumulation of fat.

The present invention also provides an amino-acid containing composition, comprising leucine in an amount of 33 to 67% by weight and threonine in an amount of 33 to 67% by weight, in terms of free amino acids thereof, based on whole amino acids.

The present invention also provides an amino-acid containing composition, comprising leucine in an amount of 33 to 50% by weight and threonine in an amount of 50 to 67% by weight, in terms of free amino acids thereof, based on whole amino acids.

The composition of the present invention can safely and effectively prevent the fat from being accumulated in the fat tissue, liver, muscles, blood and the like while reducing the risk caused by the imbalance of amino acids.

DETAILED DESCRIPTION OF THE INVENTION

Figure 1:
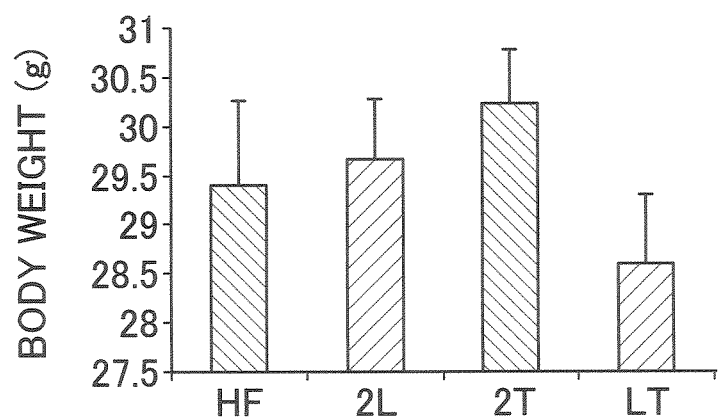
FIG. 1 is the graph showing the body weight of mice determined at the autopsy thereof in Experimental Example 1.

Threonine used in the present invention, and other amino acids such as leucine, lysine, arginine, proline or phenylalanine can be used in the present invention, as described below, may be in any forms, respectively. More specifically, each of these amino acids may be in their free acid form, or in the form of peptides, salts, solvates and the like. The term peptide herein used means a peptide where 2 to 50 amino acids, preferably 2 to 10 amino acids are bonded. It is said that the peptide is mostly converted into amino acids prior to absorption, and the peptide remaining unconverted at the absorption is fully converted into amino acids before entering the portal vein (Tadashi NOGUCHI et al., "Saishin Eiyou Kagaku (Contemporary Nutritional Chemistry)" Asakura Publishing Co., Ltd. (2004)). When these amino acids are used in the form of salts thereof, examples of the salts prepared based on the carboxyl group in their structures include ammonium salts, salts prepared in combination with alkali metals such as sodium, potassium and the like, and alkaline earth metals such as calcium, magnesium and the like, aluminum salts, zinc salts, and salts prepared in combination with organic amines such as triethylamine, ethanolamine and the like. Examples of the salts prepared based on the basic group include salts prepared in combination with inorganic acids such as hydrochloric acid, sulfuric acid, phosphoric acid and the like; organic acids such as acetic acid, citric acid, benzoic acid, maleic acid, fumaric acid, tartaric acid, succinic acid and the like; and organic sulfonic acids such as methanesulfonic acid, p-toluenesulfonic acid and the like. In the case of the solvate form, hydrates, alcohol adducts and the like can be employed. Threonine and the other amino acids such as leucine, lysine, arginine, proline or phenylalanine may be in the L-forms and DL-forms thereof. With respect to the threonine and the other amino acids such as leucine, lysine, arginine, proline or phenylalanine, two or more kinds of forms may be used in combination as a matter of course.

The composition of the present invention desirably can comprise the other amino acids in addition to threonine in an amount of 33 to 67% by weight, in terms of free amino acids thereof, based on whole amino acids. The other amino acids include leucine, lysine, arginine, proline and phenylalanine described above. When mixed with threonine, the other amino acids may be used alone or in combination with each other. Among them, a mixture with leucine and another mixture with leucine and lysine are preferable, and leucine is more preferable. The amino acids contained in the present invention are preferably in an amount of 33 to 67% by weight based on whole amino acids.

The composition of the present invention desirably comprises leucine and threonine each in an amount of 33 to 67% by weight, in terms of free amino acids thereof, based on whole amino acids.

The other amino acids may be in any forms, for example, in their free acid form, or in the form of peptides, salts, solvates and the like, similarly to threonine. The term "whole amino acid" means the total amount of amino acids in any forms, accordingly.

Preferably, leucine and threonine contained in the composition individually accounts for 30 to 140 mg, more preferably 50 to 75 mg, as a daily intake, in terms of free acids thereof, per kilogram of the body weight of a subject.

Preferably, leucine and threonine contained in the composition individually accounts for 3 to 14% by weight, more preferably 5 to 7.5% by weight, as a daily intake, in terms of free acids thereof, with respect to the daily intake of whole proteins to be ingested by a subject.

Preferably, threonine contained in the composition accounts for 30 to 140 mg, more preferably 50 to 75 mg, as a daily intake, in terms of free acids thereof, per kilogram of the body weight of a subject.

Preferably, threonine contained in the composition accounts for 3 to 14% by weight, more preferably 5 to 7.5% by weight, as a daily intake, in terms of free acids thereof, with respect to the daily intake of whole proteins to be ingested by a subject.

The following is the way how to determine the lower and upper limits of the dosages of leucine and threonine contained in the composition of the present invention based on one kilogram of the body weight of the subject, and the lower and upper limits of the contents of leucine and threonine with respect to the daily intake of whole proteins to be ingested by the subject. The lower limits are determined as the above-mentioned values on the ground that the efficacy is decreased and the significant effect is not obtained when the daily dosages of leucine and threonine are each less than 30 mg per kg of the body weight of human or the contents of leucine and threonine are each less than 3% by weight of the daily intake of whole proteins to be ingested by the subject.

The upper limits are determined with the acceptable daily intake of amino acids and safety for human taken into consideration. Although the acceptable daily intake of amino acids is not specifically established by the FDA or the like, there is a report that premature infants should not take threonine over 140 mg/kg per day, for example (J Parenteral Enteral Nutr 4: 15-17, 1980). Also, with respect to leucine, an animal experiment demonstrates that when the daily intake of leucine exceeds 20 to 25% by weight of the daily intake of total proteins, lack of appetite is induced (J. Nutr. 135: 1585S-1590S, 2005). The above-mentioned daily intake of leucine can be expressed as 200 to 250 mg per kg of the body weigh of human because the daily intake of protein is about 1 g/kg in the case of human. In light of the above, it is proper to determine the upper limit of threonine intake as a lower level from a safety standpoint. Accordingly, the daily intakes of leucine and threonine may be preferably 140 mg or less per kg of the body weight, or 14% or less by weight of the daily intake of total proteins in the case where the subject is human.

Furthermore, the way to determine the preferable range of leucine and threonine contained in the amino-acid containing composition of the invention is described below.

The inventors of the present invention conducted an experiment by feeding mice with a feed containing 20 wt. % protein. It was confirmed that increases of the body weight and the body fat were controlled and the accumulation of fat in the liver was inhibited safely and maximally when the contents of leucine and threonine added to the protein-containing feed at a meal were each 1 to 1.5% by weight with respect to the weight of the feed on a dry basis. The above-mentioned ratio corresponds to 5 to 7.5% by weight with respect to the total intake of proteins contained in the feed. Thus, the daily intakes of leucine and threonine may be preferably 50 to 75 mg/kg because the daily intake of proteins is about 1 g/kg for human.

The composition of the present invention may be put on the market in the form of a powder, a liquid mixture or the like. The composition of the present invention may be introduced commercially in the form of various products with an indication to the effect that the products are designed for inhibiting the accumulation of fat, including supplements, beverages, seasonings, processed foods, health foods, foods with nutrient function claims, drugs and the like. Needless to say, the composition of the invention can apply to foods having ordinary nutrient composition that healthy individuals eat or drink.

When commercially introduced as the supplements, the composition may be prepared into various dosage forms such as tablets, capsules, liquids, or the like, by mixing with an emulsifier, coloring agent, perfume material and the like.

The composition may be prepared into food products such as beverages, seasonings, processed foods and the like, using appropriate additives in accordance with the conventional methods. Examples of the additives may include any ingredients typically used in the conventional health foods or functional nutritional foods, such as a fruit juice for adjusting and enhancing the taste, an excipient such as dextrin or the like, a flavoring agent such as vanillin or the like, a coloring agent such as safflower or the like, cyclic oligosaccharides, saccharides (fructose, dextrose, liquid sugar, sucrose), an acidulant, powdered green tea, oils and fats, an emulsifier for enhancing the texture, collagen, whole milk powder, thickening polysaccharides, agar (when used for jelly beverage) and the like.

The food products according to the present invention may be provided as health foods or functional nutritional foods by further adding saccharides, lipids, proteins, amino acids, vitamins, in particular vitamin B2 and vitamin C, egg shell calcium, calcium pantothenate, other minerals, in particular calcium, royal jelly, propolis, honey, dietary fiber, Agaricus, chitin, chitosan, capsaicin, polyphenol, carotenoid, fatty acid, mucopolysaccharide, coenzyme, antioxidant and the like.

For obtaining the drugs, the composition of the present invention may be mixed with a pharmaceutically acceptable carrier or diluent, including cellulose derivatives such as carboxymethyl cellulose, ethyl cellulose and the like, starches such as potato starch, corn starch and the like, saccharides such as lactose, sucrose and the like, vegetable oils such as peanut oil, corn oil, sesame oil and the like, polyethylene glycol, alginic acid, gelatin, talc, etc., to prepare pharmaceutical formulations in the form of tablets, powders, pills, granules, capsules, syrups and the like for oral administration; in the injectable forms for subcutaneous injection, intravenous injection, intramuscular injection, epidural space injection, subarachnoid cavity injection, and the like; in the form of topical preparations such as nasal administration, transdermal administration, ointment and the like; in the form of suppositories such as rectal suppository, vaginal suppository and the like; in the form of drip and so on. The drugs according to the present invention can be administered orally or parenterally, for example, rectally and intravenously.

The subjects for intake of the composition according to the present invention comprising leucine and threonine may include human or animals. Examples of the animals include, but are not limited to, pets such as dogs, cats, rabbits, ferrets, hamsters, birds and the like; animals in the zoo; and domestic animals for industrial application such as horses (e.g., racehorses), cows, sheep, pigs, chickens and the like. In light of this, the composition of the present invention may be used for a feed. For example, according to the conventional methods known in the art the composition of the present invention may be prepared into an additive in a solid or liquid form that can be used for the feed.

As for the specific administration manner, the composition of the present invention can be administered as a supplement containing leucine and threonine, each at a daily dosage of 30 to 140 mg/kg of the body weight of human, or as a functional food or the like containing leucine and threonine, each at a ratio of 3 to 14% by weight of the daily intake of total proteins. The timing and frequency of administration are not particularly limited. Preferably, the composition may be taken during a meal, or before or after the meal. For example, when the amino-acid containing composition of the present invention is administered to a man weighing 60 kg, 3.6 to 25.2 g of the composition may be administered per day. When the composition is formulated in the form of a supplement or a drug, leucine and threonine are included so that composition may comprise 2 to 5 g of leucine and threonine in a unit package. About one to nine such packages may be administered per day.

EXAMPLES

Experimental Example 1

Figure 2:
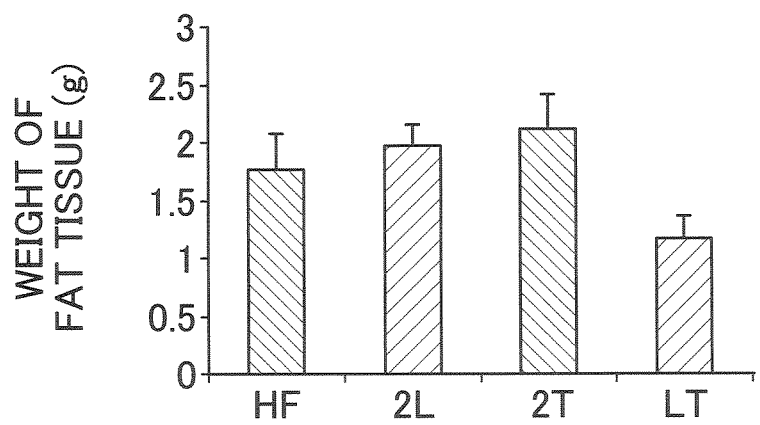
FIG. 2 is the graph showing the weight of fat tissue of the mice determined at the autopsy thereof in Experimental Example 1.
Figure 3:
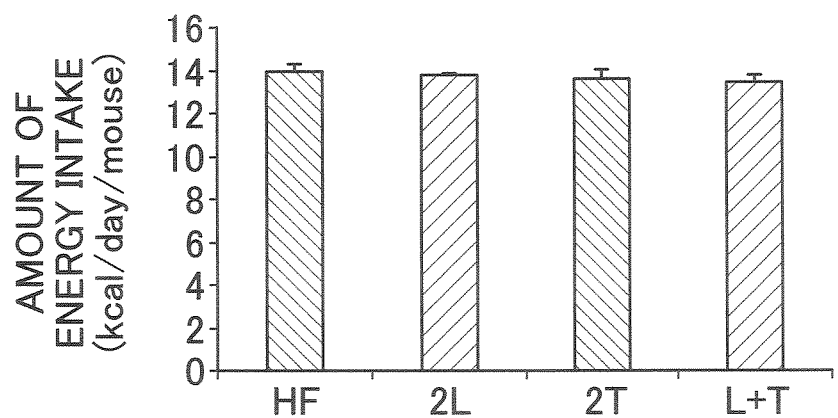
FIG. 3 is the graph showing the amount of energy intake during the feeding period in Experimental Example 1.

Forty C57BL/6J male mice (eight-weeks old, available from CLEA Japan, Inc.) were fed with CRF-1 powder (available from Oriental Yeast Co., Ltd.) during one-week acclimation period. The mice were then subjected to an experiment at the beginning of nine-weeks old. In the experiment, the mice were divided into the following four groups (ten mice/group) according to the experimental diets: (1) high-fat feed (group HF), (2) HF+2.0% L-leucine (group 2L), (3) HF+2.0% L-threonine (group 2T), and (4) HF+1.0% L-leucine+1.0% L-threonine (group LT), and fed ad libitum with water and each of the above-mentioned experimental diets for eight weeks. Table 1 shows the compositions of the four kinds of diets used in the experiment. The weight of feed intake was individually measured, and the amount of energy intake was calculated from the energy value corresponding to 1 g of each experimental feed. After the eight-weeks' experiment by feeding with the respective experimental diets, the mice were subjected to autopsy to determine their body weight, and total fat weight including the peri-epididymal fat, peri-renal fat, mesenteric fat, and subcutaneous fat around the femurs. The results are shown in FIGS. 1 to 3.

TABLE 1

| Compositions of Diets (% by weight) | | | | |
|---|---|---|---|---|
| | HF | 2L | 2T | LT |
| Casein | 20.00 | 20.00 | 20.00 | 20.00 |
| Cystine | 0.30 | 0.30 | 0.30 | 0.30 |
| Leucine | 0.00 | 2.00 | 0.00 | 1.00 |
| Threonine | 0.00 | 0.00 | 2.00 | 1.00 |
| Corn starch | 31.75 | 29.75 | 29.75 | 29.75 |
| α-corn starch | 13.20 | 13.20 | 13.20 | 13.20 |
| Palm oil | 4.00 | 4.00 | 4.00 | 4.00 |
| Soybean oil | 21.00 | 21.00 | 21.00 | 21.00 |
| Cellulose powder | 5.00 | 5.00 | 5.00 | 5.00 |
| Mixture of minerals | 3.50 | 3.50 | 3.50 | 3.50 |
| Mixture of vitamins | 1.00 | 1.00 | 1.00 | 1.00 |

TABLE 1-continued

Compositions of Diets (% by weight)

|  | HF | 2L | 2T | LT |
|---|---|---|---|---|
| Choline bitartrate | 0.25 | 0.25 | 0.25 | 0.25 |
| t-butyl hydroquinone | 0.0014 | 0.0014 | 0.0014 | 0.0014 |
| Total | 100.00 | 100.00 | 100.00 | 100.00 |

FIGS. 1 and 2 respectively show the body weight and the weight of fat tissue of the mice at the step of autopsy. As compared with the case where the HF feed is given, the body weight and the weight of fat tissue are not decreased when either leucine or threonine is added to the HF feed. In contrast to this, the group LT where the same amounts of the above-mentioned two kinds of amino acids are added to the HF feed clearly shows that accumulation of the body fat can be inhibited. These results demonstrate that the amino-acid containing composition according to the present invention is useful as a material having an inhibitory effect on the accumulation of fat. FIG. 3 shows the amounts of energy intake (i.e., kilocalories) according to the feed. There is no significant difference among the feed groups.

Experimental Example 2

Fifty C57BL/6J male mice (eight-weeks old, available from CLEA Japan, Inc.) were fed with CRF-1 powder (available from Oriental Yeast Co., Ltd.) during one-week acclimation period. The mice were then subjected to an experiment at the beginning of nine-weeks old. In the experiment, the mice were divided into the following five groups (ten mice/group) according to the experimental diets: (1) high-fat feed (group HF), (2) HF+1.5% L-leucine+1.5% L-threonine (group LT), (3) HF+3.0% amino acid composition A (group A), (4) HF+3.0% amino acid composition B (group B), and (5) HF+3.0% amino acid composition C (group C), and fed ad libitum with water and each of the experimental diets for four weeks. In accordance with the Experimental Example 1, the diets (2) to (5) were prepared by replacing a part of corn starch in the HF feed composition with the respective amino acid compositions in an amount of 3 wt. %. Table 2 specifically shows the amino acid compositions used in the groups LT, A, B and C. The amino acid compositions A, B and C are those disclosed in JP Kokai Hei 6-24977, JP Kokai Hei 4-346770, and JP Kokai Hei 9-157163, respectively.

Figure 4:
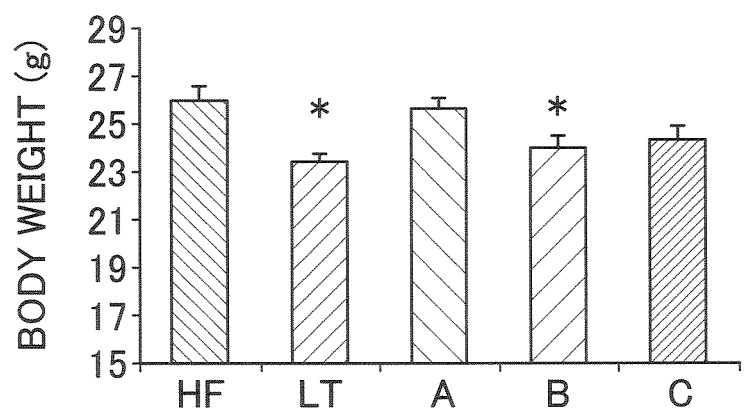
FIG. 4 is the graph showing the body weight of mice determined at the autopsy thereof in Experimental Example 2.
Figure 5:
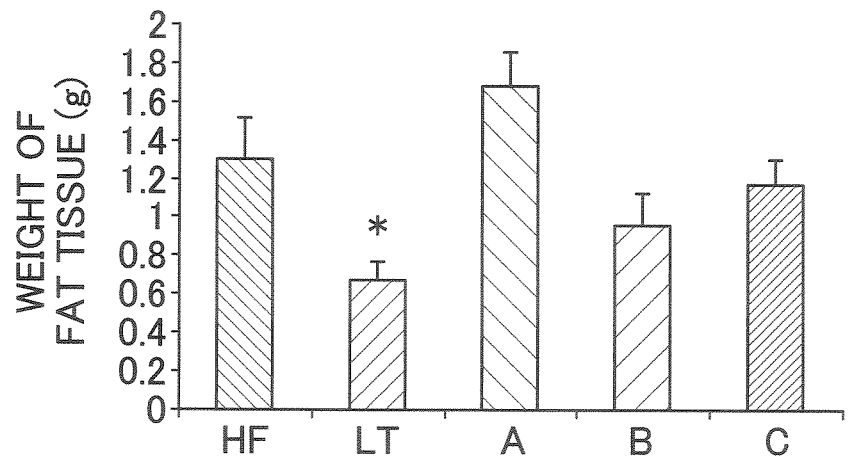
FIG. 5 is the graph showing the weight of fat tissue of mice determined at the autopsy thereof in Experimental Example 2.
Figure 6:
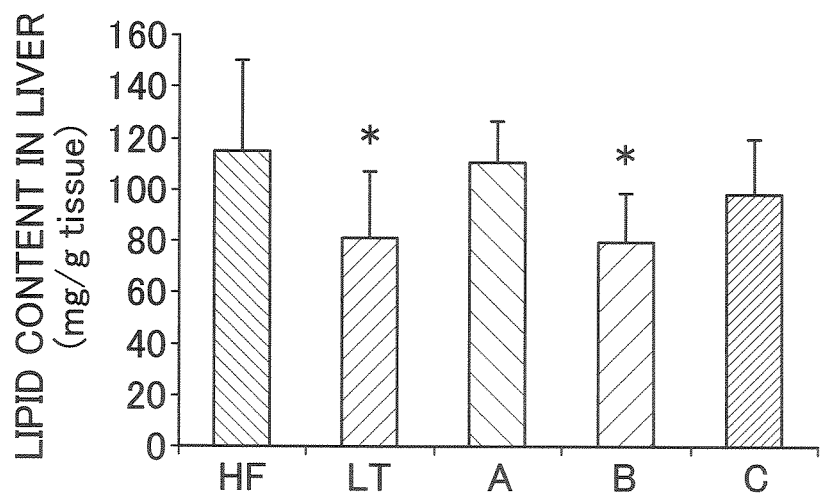
FIG. 6 is the graph showing the lipid content in the liver of mice at the autopsy thereof in Experimental Example 2.

The weight of feed intake by the individual mouse was measured, and the amount of energy intake (i.e., kilocalories) was calculated according to the feed from the energy value corresponding to 1 g of each experimental feed. After the four-weeks' experiment by feeding with the respective experimental diets, the mice were subjected to autopsy to determine their body weight, the weight of fat tissue including the peri-epididymal fat, peri-renal fat, mesenteric fat, and subcutaneous fat around the femurs, and lipid content in the liver. The results are shown in FIGS. 4 to 6.

The comparison of the group HF with each other group was made and assessed by the t-test method. In those figures, "*" means that a significant difference between the group HF and each of other groups is p<0.05.

TABLE 2

Amino-acid Compositions (% by weight)

|  | LT | A | B | C |
|---|---|---|---|---|
| Asp |  | 0.17 |  |  |
| Thr | 50.00 | 6.74 | 11.79 | 2.00 |
| Ser |  | 2.04 |  |  |
| Glu |  | 3.71 |  |  |
| Pro |  | 16.33 |  | 2.00 |
| Gly |  | 11.28 |  |  |
| Ala |  | 4.23 |  |  |
| Val |  | 5.39 | 16.54 | 2.00 |
| Met |  | 0.63 | 2.72 | 2.00 |
| Ile |  | 4.67 | 13.82 | 2.00 |
| Leu | 50.00 | 6.35 | 21.93 | 4.00 |
| Tyr |  | 8.49 |  |  |
| Phe |  | 4.99 | 9.07 | 1.00 |
| Lys-HCl |  | 12.38 | 19.83 | 1.25 |
| Trp |  | 3.53 | 4.31 | 1.00 |
| His-HCl•H$_2$0 |  | 4.25 |  | 2.70 |
| Arg |  | 4.83 |  | 79.04 |
| Gln |  | 0.00 |  | 1.00 |
|  | 100.00 | 100.00 | 100.00 | 100.00 |

Figure 7:
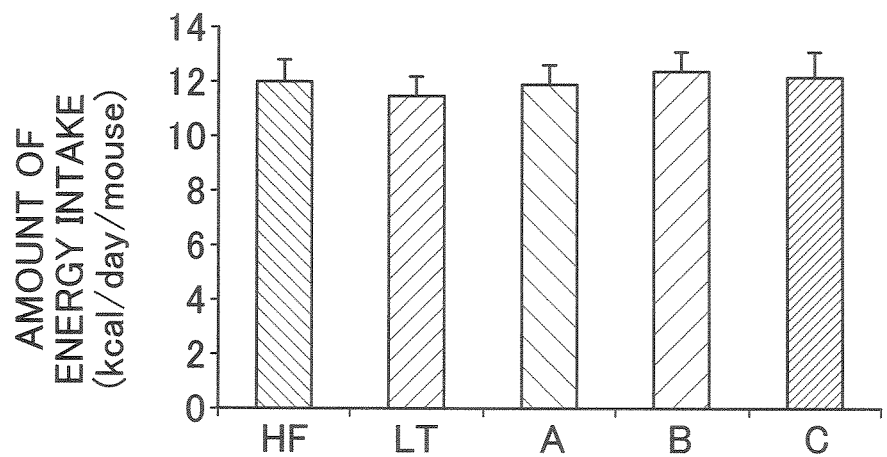
FIG. 7 is the graph showing the amount of energy intake during the feeding period in Experimental Example 2.

FIGS. 4, 5 and 6 respectively show the body weight, the weight of fat tissue and the lipid content in the liver of the mice determined at the step of autopsy. Those figures demonstrate that the amino-acid containing composition of the present invention can significantly prevent the increases in body weight, total fat weight and lipid content in the liver when compared with the conventional amino acid compositions disclosed in JP Kokai Hei 6-24977, JP Kokai Hei 4-346770, and JP Kokai Hei 9-157163. FIG. 7 shows the amounts of energy intake (i.e., kilocalories) according to the feed. There is no significant difference among the feed groups. Accordingly, the result obtained from the LT is not considered to be ascribable to the feeding deterrent effect. Although the amino acid composition B can also work to decrease the body weight and the lipid content in the liver, the group LT is superior to the group B in the inhibitory effect on the increase of the fat weight. All factors considered, the effect of the LT is more enhanced than that of the amino acid composition B.

The results of the Experimental Examples 1 and 2 demonstrate that the amino-acid composition of the present invention, characterized by comprising leucine and threonine can exhibit more enhanced inhibitory effect on the accumulation of fat when compared with the conventional amino acid compositions designed for anti-obesity.

Experimental Example 3

Figure 11:
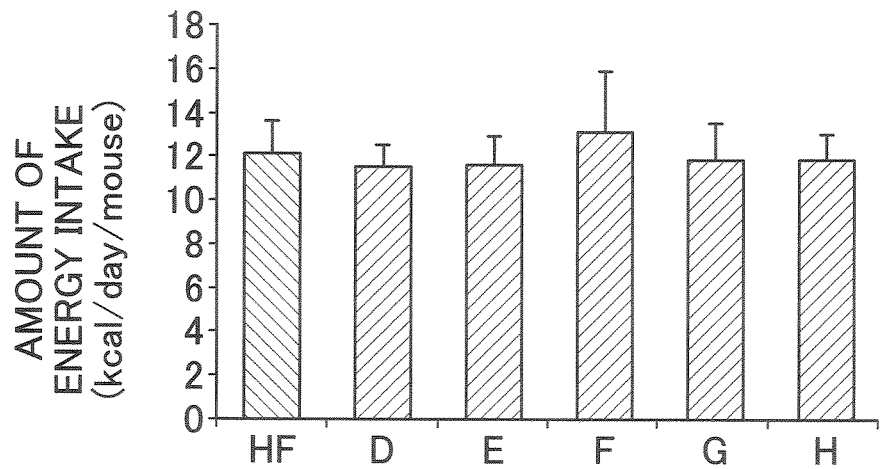
FIG. 11 is the graph showing the amount of energy intake during the feeding period in Experimental Example 3.
Figure 12:
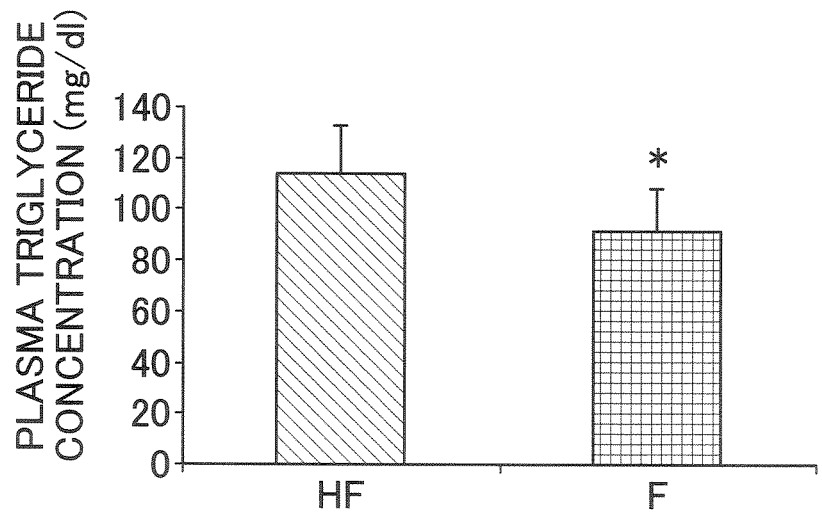
FIG. 12 is the graph showing the plasma triglyceride concentration of mice determined at the autopsy thereof in Experimental Example 3.

Sixty C57BL/6J male mice (eight-weeks old, available from CLEA Japan, Inc.) were fed with CRF-1 powder (available from Oriental Yeast Co., Ltd.) during one-week acclimation period. The mice were then subjected to an experiment at the beginning of nine-weeks old. In the experiment, the mice were divided into the following six groups (ten mice/group) according to the experimental diets: (1) high-fat feed (group HF), (2) HF+3.0% amino acid composition D (group D), (3) HF+3.0% amino acid composition E (group E), (4) HF+3.0% amino acid composition F (group F), (5) HF+3.0% amino acid composition G (group G), and (6) HF+3.0% amino acid composition H (group H), and fed ad libitum with water and each of the experimental diets for four weeks. Table 3 shows the amino acid compositions D, E, F, G and H. In accordance with the Experimental Example 1, the diets (2) to (6) were prepared by replacing a part of corn starch in the HF feed composition with the respective amino acid compositions in an amount of 3 wt. %. The weight of feed intake was individually measured, and the amount of energy intake was calculated from the energy value corresponding to 1 g of each experimental feed. After the four-weeks' experiment by feeding with the respective experimental diets, the mice were subjected to autopsy to measure their body weight; the weight of fat tissue including the peri-epididymal fat, peri-renal fat, mesenteric fat, and subcutaneous fat around the femurs; and lipid content in the liver. The results are shown in FIGS. 8 to 11. By using the amino acid composition F, which most significantly decreased the weight of fat tissue, the plasma triglyceride concentration was measured. The result is shown in FIG. 12 in which the comparison of the group HF with the composition F is made. The comparison of the group HF with each other group was made and assessed by the t-test method. In those figures, "*" means that a significant difference between the group HF and each of other groups is p<0.05. The amino acid compositions D and H that produced lower effect in terms of decreasing the weight of fat tissue than the amino acid composition F, were also subjected to the measurement of plasma triglyceride concentration and the results of which were compared with the group of HF.

TABLE 3

| Amino acid compositions (% by weight) | | | | |
|---|---|---|---|---|
| D | E | F | G | H |
| Leu | 16.7 | 33.3 | 50.0 | 66.7 | 83.3 |
| Thr | 83.3 | 66.7 | 50.0 | 33.3 | 16.7 |
| Total | 100.0 | 100.0 | 100.0 | 100.0 | 100.0 |

Figure 8:
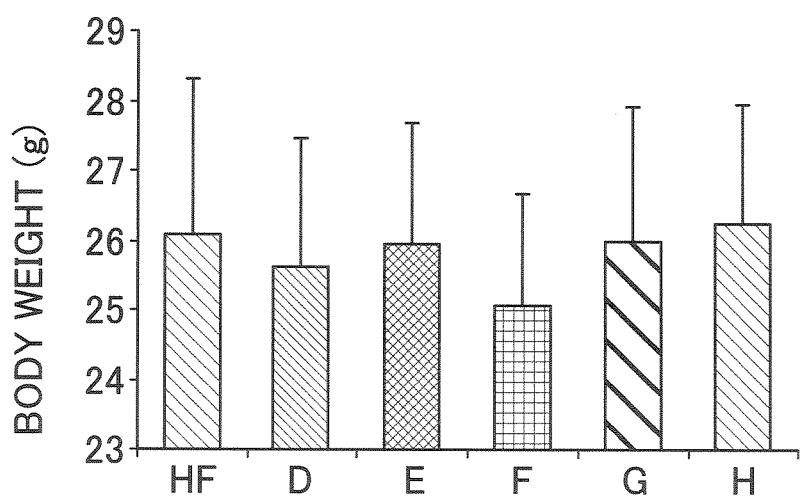
FIG. 8 is the graph showing the body weight of mice determined at the autopsy thereof in Experimental Example 3.
Figure 9:
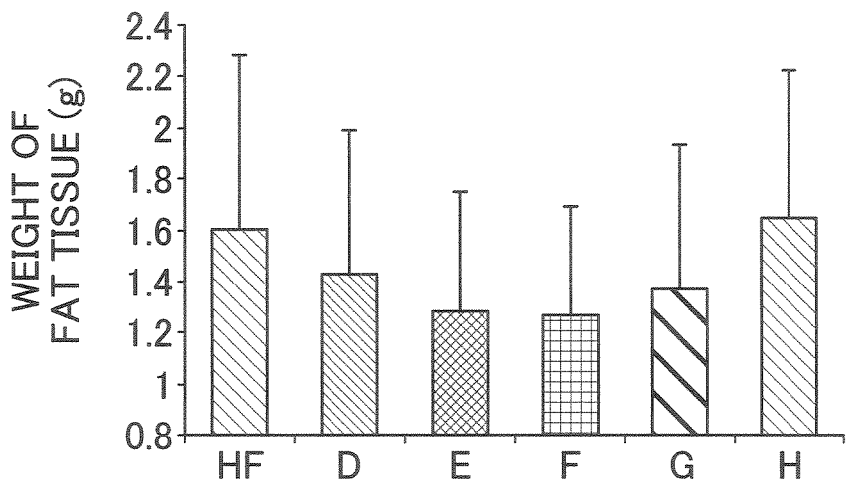
FIG. 9 is the graph showing the weight of fat tissue of mice determined at the autopsy thereof in Experimental Example 3.
Figure 10:
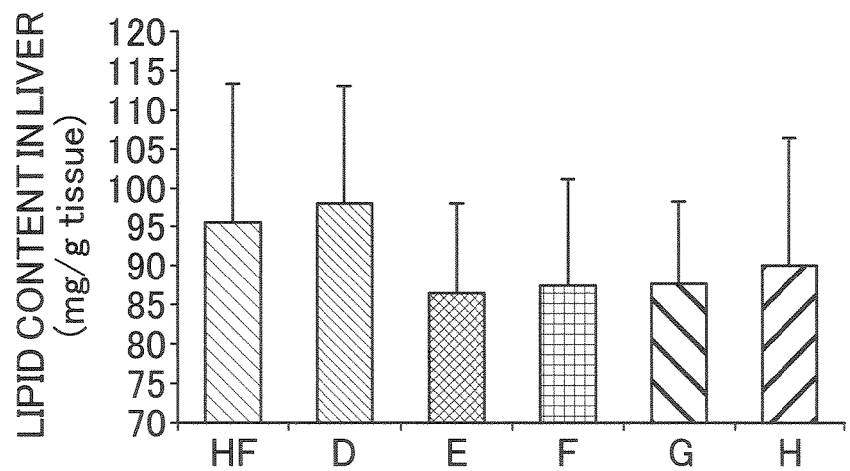
FIG. 10 is the graph showing the lipid content in the liver of mice at the autopsy thereof in Experimental Example 3.

FIGS. 8, 9 and 10 respectively show the body weight, the weight of fat tissue, and lipid content in the liver of mice, at the autopsy thereof. The largest decrease in the body weight was observed in the amino acid composition F and the amino acid composition H has a less effect on the decrease of fat weight when compared with other amino acid compositions D, E, F and G. With respect to the lipid content in the liver, the inhibitory effect on the accumulation of fat is distinct when the amino acid compositions E, F and G are employed. From these results, the amino acid compositions E, F and G are found to have more powerful inhibitory effect on the accumulation of fat than the amino acid compositions D and H, although there is an amino acid, which did not have a great impact on the accumulation of fat. This means that the best results can be obtained when the amino acid composition contains leucine in an amount of 33 to 67% by weight and threonine in an amount of 33 to 67% by weight with respect to the total weight of whole amino acids. As is shown in FIG. 11, the amount of energy intake during the feeding period was not decreased by adding the amino acid compositions. It is apparent that the accumulation of body fat is inhibited independently from feeding deterrent effect. Moreover, as is shown in FIG. 12, the decrease in plasma triglyceride concentration is significant when the amino acid composition F is used in comparison with the group HF. The plasma triglyceride concentration becomes lower in the groups where the amino acid compositions D and H are employed as compared with the case of the group HF.

Reference Example

Twenty C57BL/6J male mice (eight-weeks old, available from CLEA Japan, Inc.) were fed with CRF-1 powder (available from Oriental Yeast Co., Ltd.) during one-week acclimation period. The mice were then subjected to an experiment at the beginning of nine-weeks old. In the experiment, the mice were divided into the following two groups (ten mice/group) according to the experimental diets: (1) high-fat feed (group HF), and (2) HF+3.0% L-threonine (group 3T), and fed ad libitum with water and each of the experimental diets for eight weeks. In accordance with the Experimental Example 1, the feed (2) was prepared by replacing a part of corn starch in the HF feed composition with L-threonine in an amount of 3 wt. %.

The weight of feed intake by the individual mouse was measured, and the amount of energy intake (i.e., kilocalories) was calculated according to the feed from the energy value corresponding to 1 g of each experimental feed. After the eight-weeks' experiment by feeding with the respective experimental diets, the mice were subjected to autopsy to determine their body weight, and the weight of fat tissue including the peri-epididymal fat, peri-renal fat, and mesenteric fat. The results are shown in FIGS. 13 to 15.

Figure 13:
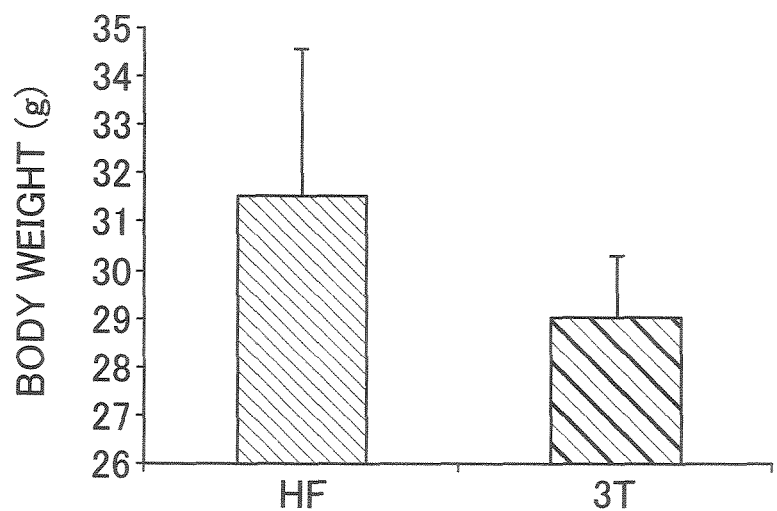
FIG. 13 is the graph showing the body weight of mice determined at the autopsy thereof in Reference Example.
Figure 14:
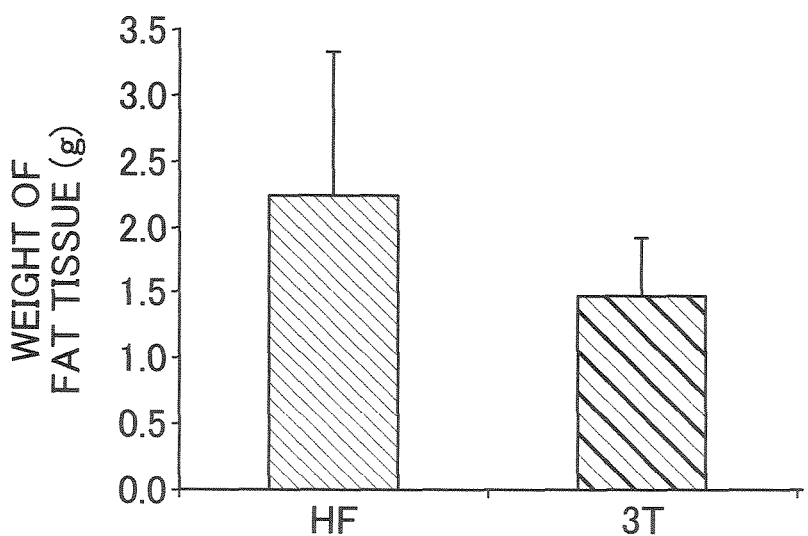
FIG. 14 is the graph showing the weight of fat tissue of mice determined at the autopsy thereof in Reference Example.
Figure 15:
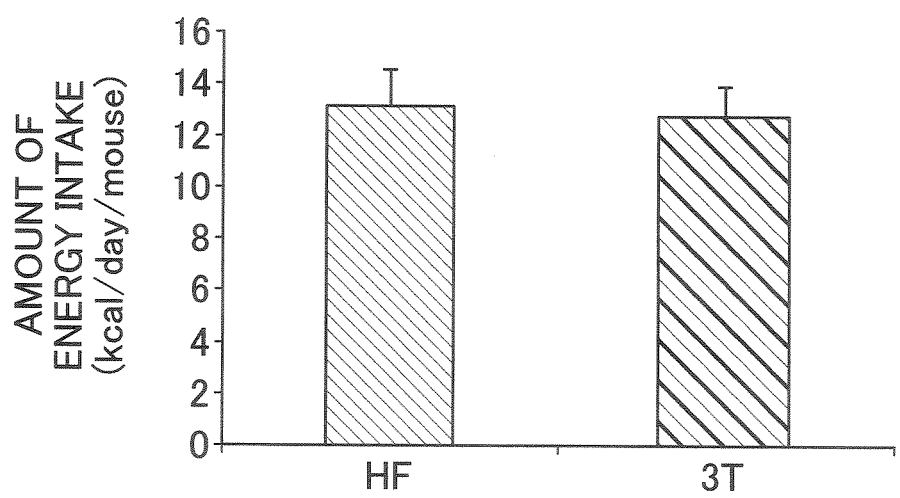
FIG. 15 is the graph showing the amount of energy intake during the feeding period in Reference Example.

FIGS. 13 and 14 respectively show the body weight and the weight of fat tissue of the mice determined at the step of autopsy. FIG. 15 shows the amounts of energy intake (i.e., kilocalories) according to the feed. As compared with the case where the HF feed is given, the body weight and the weight of the fat tissue of the mice of 3T were decreased. As is shown in FIG. 15, the amount of energy intake during the feeding period was not decreased by adding threonine. It is apparent that the accumulation of body fat is inhibited independently from feeding deterrent effect, accordingly.

What is claimed is:

1. A method for inhibiting accumulation of fat in fat tissue of a subject in need thereof, comprising administering to said subject an effective amount of the amino-acid containing composition comprising leucine in an amount of 33 to 67% by weight and threonine in an amount of 33 to 67% by weight, in terms of free amino acids thereof, based on whole amino acids, wherein said subject is a mammal or a bird.

2. The method as claimed in claim 1, wherein leucine and threonine are administered at a concentration ranging from 30 to 140 mg, individually, per day, in terms of free acids thereof, per kilogram of the body weight of the subject.

3. The method as claimed in claim 1, wherein, when the composition is administered to a subject, leucine and threonine are contained in an amount of 2 to 5 g in total in a unit package, in terms of free acids thereof.

4. The method as claimed in claim 1, wherein threonine is in a form selected from the group consisting of the free acid form, a peptide, a salt, and a solvate.

5. The method as claimed in claim 1, wherein threonine is in a peptide and said peptide has 2 to 50 amino acids.

6. The method as claimed in claim 1, wherein leucine is in a form selected from the group consisting of the free acid form, a peptide, a salt, and a solvate.

7. The method as claimed in claim 1, wherein leucine is in a peptide and said peptide has 2 to 50 amino acids.

8. The method as claimed in claim 1, wherein said fat tissues is at least one selected from the group consisting of peri-epididymal fat, peri-renal fat, mesenteric fat, and subcutaneous fat around the femur.

9. The method as claimed in claim 1, wherein said fat tissue is peri-epididymal fat.

10. The method as claimed in claim 1, wherein said fat tissue is peri-renal fat.

11. The method as claimed in claim 1, wherein said fat tissue is mesenteric fat.

12. The method as claimed in claim 1, wherein said fat tissue is subcutaneous fat around the femur.

13. The method as claimed in claim 1, wherein said subject is a mammal.

14. The method as claimed in claim 1 wherein said subject is a human.

15. The method as claimed in claim 1, wherein said subject is an animal selected from the group consisting of a dog, a cat, a rabbit, a ferret, a hamster, a bird, a zoo animal, a horse, a cow, a sheep, a pig, and a chicken.

16. The method as claimed in claim 1, wherein said subject is a bird.

* * * * *